United States Patent [19]
Fleissner

[11] Patent Number: 5,625,962
[45] Date of Patent: May 6, 1997

[54] METHOD FOR MEASURING THE MOISTURE CONTENT OF A WEB OF GOODS ON A THROUGH-FLOW DRYER AND DEVICE FOR WORKING THE METHOD

[75] Inventor: Gerold Fleissner, Zug, Switzerland

[73] Assignee: Fleissner GmbH & Co., KG, Egelsbach, Germany

[21] Appl. No.: 298,282

[22] Filed: Aug. 31, 1994

[51] Int. Cl.$^6$ ............................................. F26B 3/00
[52] U.S. Cl. ..................... 34/446; 34/491; 34/495; 34/528
[58] Field of Search .................. 34/446, 485, 491, 34/493, 495, 528, 535, 570, 571

[56] References Cited

U.S. PATENT DOCUMENTS

| | | | |
|---|---|---|---|
| 3,338,411 | 8/1967 | Von der Gathen et al. | 34/491 |
| 3,363,326 | 1/1968 | Weeks | 34/528 |
| 4,204,337 | 5/1980 | Roos et al. | 34/446 |

FOREIGN PATENT DOCUMENTS

| | | | |
|---|---|---|---|
| 3239250 | 4/1984 | Germany | 34/446 |

*Primary Examiner*—F. Daniel Lopez
*Attorney, Agent, or Firm*—Antonelli, Terry, Stout & Kraus, LLP

[57] ABSTRACT

The position of the exhaust air flap of a through-flow dryer, for example, a screen drum dryer, is adjusted to determine the moisture content of the exhaust air. This is advantageously accomplished as a function of the desired drying temperature of the goods or their moisture content when the good leaves the dryer. Provision is made according to the invention to measure the temperature of the air after passing though the web, at least in the vicinity of the outlet of the dryer, to relate it to the temperature of the ambient air and thus to determine the temperature of the goods and hence their moisture content, since in the residual drying range, the moisture content of the goods is a function of the temperature of the goods. The exhaust air moisture content can then be regulated with this measured value.

5 Claims, 1 Drawing Sheet

METHOD FOR MEASURING THE MOISTURE CONTENT OF A WEB OF GOODS ON A THROUGH-FLOW DRYER AND DEVICE FOR WORKING THE METHOD

BACKGROUND OF THE INVENTION

Use of a plurality of through-flow dryers to dry a web of textile or paper goods is known. First among these dryers are the screen or sieve drum dryers according to DE-OS 16 04 784, as well as the belt dryers according to DE 29 50 295 A1. It is known to determine the temperature of the ambient air flowing over the goods to be dried by means of thermocouples located in the dryer and to use these measured values to regulate the heating assemblies, taking the incoming air into account in the heating power (DE-OS 16 04 784). It is also known to regulate the fan of a screen drum unit that accelerates the processing air, specifically as a function of the pressure differential between the outside of the screen drum and after the air has passed through the web (DE-OS 16 35 357).

However, the method according to the present invention involves regulating the moisture content of a web to be dried with through ventilation. For this purpose, according to the ITS publication "Farberei/Druckerei/Ausrustung" 3/1967, pages 14–26, especially page 26, it is possible to measure the residual moisture content of a web with electrical auxiliary devices. Measuring devices of this kind however only operate up to hygroscopic equilibrium of the respective goods; they are also inexact and therefore operate unsatisfactorily. To avoid these problems, it is possible to overdry a web and then moisten it again to the desired moisture content. This procedure is uneconomical, however.

A device is known with which the moisture content is measured over the width of the web at the outlet from the dryer, and the exhaust air flap of the dryer is regulated by this measured value. During this measurement process, an infrared measuring head moves transversely across the web. This moisture measurement provides good results, but it is too costly in terms of the cost of the apparatus and hence it is too expensive.

SUMMARY OF THE INVENTION

One goal of the invention is to provide a method for achieving moisture content measurement that always operates precisely, which uses a device that is very economical to manufacture, and which can also always determine exactly the point at which the web becomes dry during the drying process.

Taking its departure from a method for measuring moisture content in a web to be dried, for example, a paper web or nonwoven fabric web, in order to regulate one or more drying parameters of a continuous dryer in which the web is ventilated transversely, the invention provides for achieving the stated goal by measuring the temperature of the treating air before the air passes through the web, and after the air passes through the web, at several points over the length of the drying path and the temperature of the web is obtained by comparing the temperatures on both sides of the web at a given point of time in the drying process, hence also determining the actual moisture content in the goods at this point in time, and then, on the basis of the moisture content measured in this manner by thermocouples or similar temperature-measuring assemblies, regulating one or another drying parameter in the dryer.

The idea that forms the basis of this measurement method consists in the fact that the goods forming the web to be dried pass through a very characteristic temperature curve as they dry that is known of itself. When the temperature of the textile material, nonwoven fabric for example, is measured during drying, it initially rises sharply in the heating zone of the dryer. When the cooling limit temperature is reached, a physical state is created in which the warmer air reduces the moisture content of the textile material, but the textile material cannot heat up any further because the energy from the warmer air is changed into heat of evaporation. The temperature of the nonwoven fabric behaves differently at the end of the drying process. As drying slows down, the temperature of the nonwoven fabric rapidly rises to the temperature of the drying air during residual evaporation. In this residual evaporation area, the temperature of the nonwoven fabric can be used to determine the moisture content in the nonwoven fabric. Each temperature after passing through the nonwoven fabric temperature with a computation factor, corresponds to a moisture content that is specific to the textile material. The moisture content characteristic of the respective textile material or nonwoven fabric is determined in experiments and recorded in a log. It is better to enter the data determined for each material into a computer, so that new, modified conditions of a known material can be called up at any time.

Any state of dryness of a textile or paper material can be produced with the method according to the invention. If an overdried textile material is desired, the drum dryer is controlled in such fashion that the point of complete drying, at which the temperature of the air after passing through is equal to the temperature of the incoming air, is at a point on the drum which is at a distance from the outlet of the dryer. The dryer then has a performance reserve. By using the latter, for example, an applied binder can be vulcanized. If it is desired to have the textile material just dry, the point of complete drying, in other words determination of the temperature differential between the outside and inside of the drum, should be located a short distance before the textile material is removed from the drum. However, if the material must be delivered with a certain amount of residual moisture still in it, the temperature measured inside the drum, for example, at the point where the goods leave the drum, must be lower than that of the incoming air. The temperature to be measured at the outlet inside the drum, based on a certain moisture content of the material, is material-specific. These data can be readily ascertained in the laboratory.

A device for working the method of this invention is easy and economical to manufacture. Several thermocouples are mounted in the vicinity of the sieve or screen drum, both outside the drum or the like and inside the drum, and connected with a computer that determines the temperature differential and takes it into account together with a corresponding moisture content defined earlier. Conversely, the desired moisture content of a web can be entered into the computer at a certain point in the drying process, with the computer then determining one or more drying parameters and regulating the drying process. It is, therefore, advantageous to regulate the open position of the exhaust air flap connected to an exhaust air duct of the dryer.

In the accompanying drawing, the method according to the invention is explained with reference to a screen drum dryer.

Figure 2:
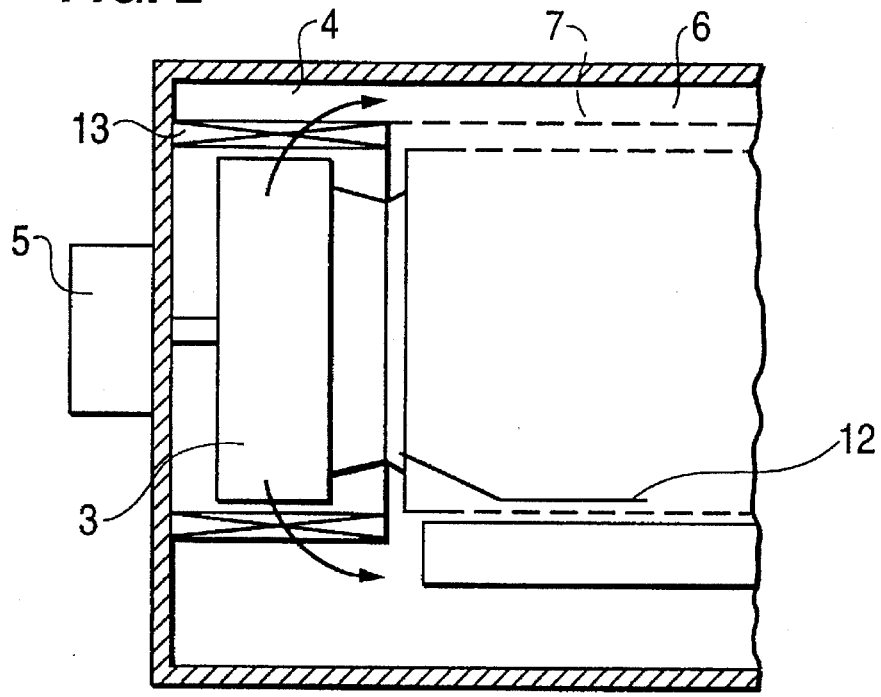
FIG. 2 is the screen drum device according to FIG. 1 in a lengthwise section.

The screen drum device consists of a heat-insulated housing 1, in which a screen drum 2 is rotatably mounted. At one end of the screen drum 1 in this example, the fan 3 shown in FIG. 2 is located in a separate fan chamber 4 and produces a vacuum inside the screen drum 2. Fan 3, driven by motor 5, blows the processing air from all sides in the direction of the arrows, around the screen drum into treatment chamber 6, separated by a screen cover from the screen drum to blend the air flow. Immediately below screen drum 2, which is wrapped 75% by the web, a reversing roller 9 is located that delivers the web of textile material 10 onto an endless belt 16. This belt is advisable for post-fixing processing of the textile material, but it can also be omitted so that the textile material is delivered immediately to outside of the housing from deflecting roller 9. The air accelerated by fan 3 initially passes through heating devices 13 located above and below the fan and shown in FIG. 2, so that a constant temperature can be maintained in processing chamber 6.

Figure 1:
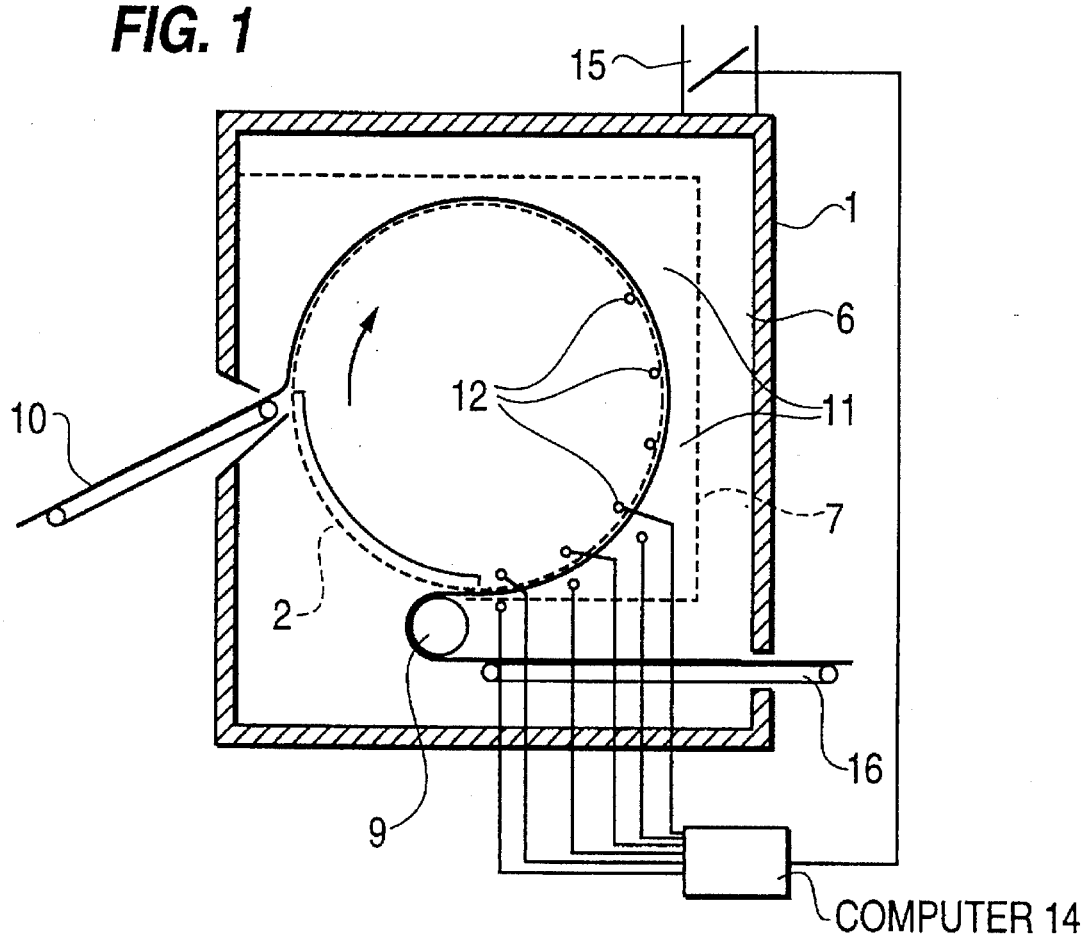
FIG. 1 is a cross section of a screen drum device with only one drum.

The temperature outside screen drum 2 is measured by temperature sensors 11. They are mounted at the same height around drum 2. After passing through a web 10 to be dried, because of the draft created by fan 3, the temperature of the air has cooled off somewhat, and is measured by means of temperature sensors 12 and transmitted to the outside through sliding contacts. The temperature sensors inside and outside are located exactly radially opposite one another. A computer 14 shown in FIG. 1 is supplied with the values measured by the temperature sensors 11 and 12, and then regulates the inclination of exhaust air flap 15, for example, to control the volume of the exhaust and hence its moisture content. (The lines connecting the temperature sensors 11 and 12 at the upper part of the drum to the computer in FIG. 1 are not shown to simplify understanding of the drawings).

The moisture content of the goods must be determined at a measurement location after an exact measurement of the temperature. Since this conclusion naturally must be checked, as it depends on the nature of the goods, the actual moisture content must be measured at this point or tested by an appropriate procedure in the laboratory. A sample of the web is collected and an actual moisture content is determined by weighing prior to drying in the dryer. Also, relationships determined in tests between the temperature of the web in the dryer and the moisture content of the web outside the dryer determined by weighing, based on certain quantity of goods, are entered into the computer and used for continuously regulation of the drying process of the through-flow dryer. This is done for each type of goods and the information is entered into the computer. Therefore, when a value for the moisture content is determined by the indirect measurement according to the invention, the accuracy of this value is checked based on the data previously obtained by direct measurement in the laboratory and a correction factor, which is specific for the goods, is added if required.

If it is desired to obtain goods from the dryer that are just 100% dry, and the required moisture content at a certain point in the dryer has been determined, so that at the moisture content still existing at that point, the goods will be delivered dry when they have passed through the remaining stretch of the dryer, the drying process is functioning correctly. However, if the computer measures a higher goods temperature at this point and therefore concludes that the moisture content is less, the fan is running too fast or the heater is set too high or the rotational speed of the drum is too slow. One or more of the drying parameter is adjusted so that the goods emerge from the dryer, just 100% dry. The temperature usually is measured at only one given point in time in the dryer and the moisture content of the goods is determined at this point in time. If the goods are too dry at this point, the heat is turned down, for example, so the goods are just dry when they emerge.

What is claimed is:

1. A method for controlling the drying of an endless web of textile or paper material in a continuous through-flow dryer by regulating one or more drying parameters, which comprises passing heated and dried air transversely through the web to dry the web conveyed on a perforated surface, measuring temperature of the heated air, immediately before passing through the web and immediately after passing through the web, at several points over a length of a drying path on the perforated surface, and determining a temperature of the web indirectly and hence actual moisture content in the web at each of said several points by comparing air temperatures on both sides of the web at each of said several points along the drying path, and regulating at least one drying parameter in the dryer on the basis of the moisture content measured in this manner.

2. A method for effecting more exact measurement of moisture content in a web of textile or paper material, wherein a sample of the web is collected and an actual moisture content is determined by weighing the sample in a laboratory prior to drying the web in the dryer, in the method according to claim 1, wherein the moisture content based on the dry weight of the sample per unit area prior to drying the web in the dryer is compared with the two temperatures of the heated air before and after passing through the web after the web has been conveyed over the drying path and when a through-flow drying process in the dryer is over and by controlling a drying parameter, the temperature of the dried web and a desired moisture content of the web delivered outside the dryer are regulated.

3. A method according to claim 2, wherein volume of exhaust air and humidity in the dryer are regulated and an open position of an exhaust flap of the dryer is regulated as a function of temperature measurements to control said drying parameter.

4. A method according to claim 3, wherein relationships determined in tests between a temperature of the web in the dryer and moisture content of the web outside the dryer determined by weight, based on a certain quality of goods, are entered into a computer and used for continuous regulation of the drying process of the through-flow dryer.

5. A device for performing the method according to claim 1, with a heat-treatment assembly in which a stream of the heated and dried air is passed transversely through the web to be dried, characterized by comprising a plurality of temperature sensors provided at said several points in the flow direction of the air behind the web over the length of the drying path and a plurality of other temperature sensors for measuring the temperatures of the air prior to passing through the web, a device for comparing the temperatures measured behind the web with the temperatures of the air measured prior to passing through the web, and thus effecting determination of the temperatures of the web itself at said several points and computer means for evaluating the temperatures of the web thus obtained in a zero-contact manner to determine the moisture contents of the web at said several points on the basis of the knowledge of the moisture characteristics of the web determined by preliminary tests in a laboratory.

\* \* \* \* \*